United States Patent
Baan et al.

(10) Patent No.: US 7,183,434 B2
(45) Date of Patent: Feb. 27, 2007

(54) PROCESS FOR THE CONTINUOUS QUATERNIZATION OF TERTIARY AMINES WITH AN ALKYL HALIDE

(75) Inventors: Willem Hendrikus Baan, Nijbroek (NL); Jacobus Van Den Berg, Voorthuizen (NL)

(73) Assignee: Akzo Nobel N.V., Arnhem (NL)

( * ) Notice: Subject to any disclaimer, the term of this patent is extended or adjusted under 35 U.S.C. 154(b) by 183 days.

(21) Appl. No.: 10/499,132

(22) PCT Filed: Dec. 5, 2002

(86) PCT No.: PCT/EP02/13755

§ 371 (c)(1),
(2), (4) Date: Sep. 28, 2004

(87) PCT Pub. No.: WO03/053908

PCT Pub. Date: Jul. 3, 2003

(65) Prior Publication Data

US 2005/0020474 A1    Jan. 27, 2005

(30) Foreign Application Priority Data

Dec. 21, 2001    (SE) .................................. 0104346

(51) Int. Cl.
*C07C 209/00*    (2006.01)

(52) U.S. Cl. .................................................. 564/296

(58) Field of Classification Search ................. 564/296
See application file for complete search history.

(56) References Cited

U.S. PATENT DOCUMENTS

| | | | |
|---|---|---|---|
| 3,557,214 A * | 1/1971 | Koenig et al. ............... | 564/296 |
| 3,813,441 A | 5/1974 | Muller-Schiedmayer et al. ...................... | 260/567.6 |
| 4,275,235 A | 6/1981 | Giede et al. ................ | 564/288 |
| 5,041,664 A | 8/1991 | Su ............................... | 564/296 |
| 5,196,582 A * | 3/1993 | Smith et al. ................ | 564/292 |
| 5,260,480 A | 11/1993 | Lacroix et al. ............. | 560/222 |
| 5,491,240 A | 2/1996 | Arnold et al. ........... | 548/347.1 |
| 5,599,990 A | 2/1997 | Miller et al. ................ | 564/296 |

FOREIGN PATENT DOCUMENTS

| | | |
|---|---|---|
| EP | 0288857 A2 | 11/1988 |
| EP | 0468638 A1 | 1/1992 |
| EP | 0869114 A1 | 10/1998 |
| GB | 2232980 A | 1/1991 |
| WO | WO 00/43348 | 7/2000 |

OTHER PUBLICATIONS

Almarzoqi et al., Tetrahedron (1986), 42(2), p. 601-607.*
International Search Report No. PCT/EP02/13755; Completed on Mar. 27, 2003.
Abstract of EP 288857, (1988).
Abstract XP-002236250, (abstract of CN 126367A Dec. 13, 2000).

* cited by examiner

*Primary Examiner*—Brian Davis
(74) *Attorney, Agent, or Firm*—Ralph J. Mancini

(57) ABSTRACT

The present invention relates to a continuous process for the quaternization of tertiary amines with an alkyl halide. The process is performed at a temperature between 50° C. and 140° C. by reacting a tertiary amine and an alkyl halide in a tubular reactor at a pressure sufficient to keep the alkyl halide dissolved in the reaction mixture. The molar ratio between the tertiary amine and the alkyl halide is from 1:1.3 to 1:2.9 and the pressure is suitably between 12 to 65 bar. The process could be performed either with or without a solvent present, preferably without a solvent. The process gives high product yields and low amounts of by-products.

8 Claims, No Drawings

PROCESS FOR THE CONTINUOUS QUATERNIZATION OF TERTIARY AMINES WITH AN ALKYL HALIDE

This case was filed under the Patent Cooperation on Dec. 5, 2002 as International Application No. PCT/EP02/13755, and claims priority of Swedish application No. 0104346-2 filed on Dec. 21, 2001.

The present invention relates to a continuous process for the quaternisation of tertiary amines with an alkyl halide that is dissolved in the reaction mixture.

Several methods for quaternisation of amines with alkyl halides have been disclosed. The quaternisation processes are performed within a variety of pressure and temperature ranges, and at different molar ratios between the amine and the quaternising agent. There are included embodiments both of batch-wise as well as continuous processes.

In EP 0 869 114 a quaternisation process is described where an alkoxylated ester-amine is reacted with a quaternising agent at a pressure of 1–50 bars. The process is batch-wise, and in the working examples the process is performed in a low-pressure autoclave with 1.025 mole methyl chloride per mole ester-amine during 24 hours or more.

In U.S. Pat. No. 3,813,441 a continuous process for the manufacture of quaternary ammonium chlorides is described, where a primary or a secondary amine is reacted with methyl chloride at a temperature of 50–80° C. and at a pressure of 3 to 10 atm. The reaction is performed in the presence of an aqueous solution of an alkali metal hydroxide and a lower alcohol. Since a primary or secondary amine is the starting material, sodium chloride is formed during the reaction and has to be removed continuously.

U.S. Pat. No. 5,491,240 discloses in the working examples a batch process for the manufacture of a quaternary ammonium compound by reacting a tertiary amine stepwise with a quaternising agent, e.g. methyl chloride, at a pressure of maximum 62 psig (about 5.3 bar) during reaction times of about 10 hours. Solvent is added intermittently if the viscosity gets too high, to maintain the reaction mixture in the liquid state during the reaction.

EP 0 288 857 describes a quaternisation reaction between a tertiary amine and an alkyl halide present in a molar ratio ranging from 1:3 to 1:8 at a temperature between 50–150° C. at an over-pressure (18 and 27.5 bar in the examples). The reaction is performed batch-wise in the absence of solvents, and the quaternary ammonium compound is obtained in powdered form. The reaction time stated in the examples was about 2 hours. EP 0 012 296 and U.S. Pat. No. 4,275,235 describe a similar process using the same molar ratio range.

In U.S. Pat. No. 5,041,664 a continuous quaternisation process is disclosed where a long chain tertiary amine and an alkyl chloride are reacted in the presence of a heterogeneous catalyst in the presence of an alcohol solvent. The mole ratio between the amine and the chloride is suitably 1:1.2 to 1.2:1, preferably 1:1, and the pressure may be from about 1 to 210 bar. In the working example 70 bar is used.

The aim of the present invention is to create a continuous process for the manufacture of quaternary ammonium compounds from tertiary amines and alkyl halides, which is performed at moderate pressures and temperatures, and with short reaction times and no need for solvents, nor for catalysts. The process should also give high product yields and low amounts of by-products.

It has surprisingly been found that these objects can be fulfilled by a continuous process for manufacturing a quaternary ammonium compound by reacting, at a temperature between 50° C. and 140° C., preferably from 70° C. to 130° C. and most preferably from 80° C. to 125° C., a tertiary amine and an alkyl halide in a tubular reactor at a pressure sufficient to keep the alkyl halide dissolved in the reaction mixture, preferably at 12–65 bar, more preferably at 15–55 bar and most preferably at 18–50 bar, the molar ratio between the tertiary amine and the alkyl halide being from 1:1.3 to 1:2.9, preferably from 1:1.4 to 1:2.7 and most preferably from 1:1.5 to 1:2.6. The process could be performed either with or without a solvent present, preferably without a solvent.

There are several advantages connected with the process of the present invention.

Firstly, by using a pressure between 12 and 65 bar within the given temperature interval, the alkyl halide will be present in a solution together with the tertiary amine reactant, the quaternary ammonium product formed during the reaction and optionally a solvent. Thereby the viscosity of the reaction mixture will be reduced. The reaction may even be performed without any solvent, which will lead to less by-product formation. To use a pressure above 65 bar will not give any additional advantages during the present conditions. No significant increase in the reaction rate will be achieved, and such a high pressure will require more expensive equipment. The optimal pressure depends for example on the temperature and the type of alkyl halide chosen, but is normally from 18 to 30 bar for a reaction performed in a solvent, and normally from 30 to 50 bar for a solvent-free process. When a solvent, such as an alcohol, is present during the quaternisation process, by-products, such as ethers, may be formed from the solvent and the alkyl halide. When recycling the unreacted alkyl halide, there will normally be a build-up of these by-products that may cause severe problems in the commercial production process, as well as for the quality of the desired quaternary ammonium products.

Secondly, by using a molar ratio of tertiary amine to alkyl halide between 1:1.3 and 1:2.9, there will be a smaller volume of the reactor occupied by the alkyl halide and a smaller amount of alkyl halide to recycle as compared to the process described in the working examples in EP 0 288 857, where the ratio is 1:3.4.

Thirdly, a continuous process according to the invention, which results in a short residence time and makes optimal use of the available reactor space, will give rise to a higher space time yield and a better quality of the product, such as low colour.

Preferably the reaction mixture is blended with the aid of internals in the tubular reactor. The presence of internals promotes plug-flow behaviour of the reaction mixture, and will further increase the reaction rate and the production capacity of the tubular reactor. Suitable internals are for example an inert packing, such as glass raschig rings.

The temperature according to the invention varies within the range of 50 to 140° C. At temperatures below 50° C. the reaction rate is not sufficient, and above 140° C. there is too much decomposition of the quaternary ammonium salt and formation of by-products. The temperature range is normally between 80 and 125° C.

The quaternary ammonium compounds that may be manufactured by the process of the present invention could have the formula $$R_1R_2R_3R_4N^+X^-  \qquad (I)$$

where $R_1$ is a hydrocarbyl group containing 1–22 carbon atoms, preferably 1–4 carbon atoms; $R_2$ and $R_3$ are the same or different hydrocarbyl groups containing 1–22 carbon atoms, preferably 8–22 carbon atoms, which could be saturated or unsaturated, linear or branched, or a group $(AO)_yH$ where AO is an alkyleneoxy group with 2 or 3 carbon atoms, preferably 2 carbon atoms, and y is a number between 1–50; $R_4$ is an alkyl group containing 1–4 carbon atoms, preferably 1–2 carbon atoms; $X^-$ is a halide anion, preferably $Cl^-$, $Br^-$ or $I^-$ and most preferably $Cl^-$. These quaternary compounds are obtainable by the process of the present invention by reacting a tertiary amine of the formula $R_1R_2R_3N$ with an alkyl halide of the formula $R_4X$, where X is halogen and $R_1$, $R_2$, $R_3$ and $R_4$ have the same meaning as in formula I. Suitable examples of the tertiary amines are di(tallow alkyl)methylamine, (tallow alkyl)dimethylamine, di(hydrogenated tallow alkyl)methylamine, (hydrogenated tallow alkyl)dimethylamine, di(rape seed alkyl)methylamine, (rape seed alkyl)dimethylamine, di(soya alkyl)methylamine, (soya alkyl)dimethylamine, di(coco alkyl)methylamine, (coco alkyl)dimethylamine, distearylmethylamine, stearyldimethylamine, dilaurylmethylamine, lauryldimethylamine, polyethoxylated primary amines, such as polyethoxylated cocoamine, polyethoxylated (tallow alkyl)amine and polyethoxylated (hydrogenated tallow alkyl)amine and polyethoxylated secondary amines, such as polyethoxylated dicocoamine, polyethoxylated di(tallow alkyl)amine and polyethoxylated di(hydrogenated tallow alkyl)amine.

Other quaternary ammonium compounds that may be formed by the process of the present invention have the formula

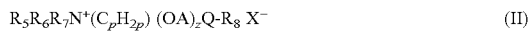

$$R_5R_6R_7N^+(C_pH_{2p})(OA)_zQ\text{-}R_8\ X^- \quad (II)$$

where $R_5$ and $R_6$ independently is an alkyl group containing 1–6 carbon atoms, preferably 1–4 carbon atoms and most preferably 1–2 carbon atoms; $R_7$ is —$(C_pH_{2p})(OA)_zQ\text{-}R_8$ or a hydrocarbyl group with 1–22 carbon atoms, preferably 1–6 carbon atoms, more preferably 1–4 carbon atoms and most preferably 1–2 carbon atoms; $R_8$ is a hydrocarbyl group with 1–22 carbon atoms, preferably 8–22 carbon atoms; Q is

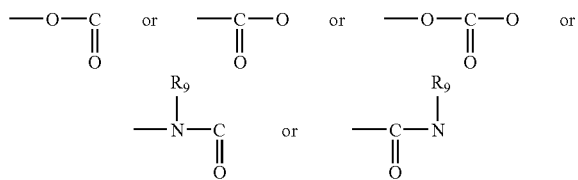

p is a number from 1 to 6, preferably 2–3, OA is an oxyalkylene group with 2 or 3 carbon atoms, preferably 2 carbon atoms, z is a number between 0 and 50; $R_9$ is H or a hydrocarbyl group with 1–22 carbon atoms and $X^-$ has the same meaning as in formula I. $R_8$ and $R_9$ could be saturated or unsaturated, linear or branched. The products of formula II include the so-called esterquats. These are obtainable by the process of the present invention by reacting a tertiary amine of formula $R_6R_7N(C_pH_{2p})(OA)_zQ\text{-}R_8$ with an alkyl halide of the formula $R_5X$, where Q is —C(=O)—O— or —O—C(=O), X is halogen and $R_5$, $R_6$, $R_7$, $R_8$, p, OA and z have the same meaning as above. Suitable examples of these tertiary amines are the diesters of stearic acid, coco fatty acid, tallow fatty acid, rape seed fatty acid, soya fatty acid, oleic acid, palmitic acid or lauric acid and methyldiethanolamine. Also included are the amidoquats, which are obtained in an analogous manner from a tertiary amine according to the above formula where Q is —N($R_9$)—C(=O) or —C(=O)—N($R_9$). Suitable examples of these tertiary amines are the amidoamines obtained from N,N-dimethylpropylenediamine and a fatty acid such as stearic acid, coco fatty acid, tallow fatty acid, rape seed fatty acid, soya fatty acid, oleic acid, palmitic acid or lauric acid.

Still another group of quaternary ammonium compounds that may be obtained by the process of the present invention has the formula

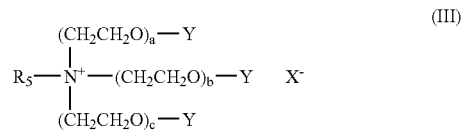

where each Y independently is H or —C(=O)—$R_8$, $\Sigma a+b+c$ is 3–50 and $R_5$, $R_8$ and $X^-$ have the same meaning as above. These quaternary ammonium compounds are esterquats that are obtainable by the process of the present invention from fatty acid esters of triethanolamine or ethoxylated triethanolamine and an alkyl halide $R_5X$, where X is halogen and $R_5$ has the same meaning as in formula III. Suitable examples are the esters obtained from triethanolamine or ethoxylated triethanolamine and an acid selected from the group stearic acid, coco fatty acid, tallow fatty acid, rape seed fatty acid, soya fatty acid, oleic acid, palmitic acid and lauric acid.

The compounds that may be quaternised by the process of the present invention are not limited to the types mentioned above. For example, also tertiary amines selected from the group consisting of di- and polyamines, alkoxylated di- and polyamines, 3-alkyloxypropylamines, alkoxylated 3-alkyloxypropylamines, N-(3-alkoxypropyl)-1,3-propanediamines, alkoxylated N-(3-alkoxypropyl)-1,3-propanediamines, amidoamines and amino acids may be quaternised. The only requirement is that the compound to be quaternised should contain a tertiary amino group and no primary or secondary amino groups.

The alkyl halide used as the quaternising agent is preferably methyl chloride, methyl bromide, ethyl chloride or ethyl bromide, and most preferably methyl chloride.

The following examples are illustrative of the invention, and should not be construed as limiting thereof.

EXAMPLE 1

A 0.4 l tubular reactor with an internal diameter of 0.01 m, filled with an inert packing consisting of glass raschig rings, was used for the continuous reaction of 68 g/hour di(hydrogenated tallow alkyl)methylamine/isopropanol mixture with methyl chloride. The reactant tertiary amine/methyl chloride molar ratio was 1:1.6 (MW amine=523) and the isopropanol content was 15% counted on tertiary amine. During the quaternisation the reactor temperature was kept at 100° C. and the reactor pressure was 20 bar. The resulting product was depressurized and collected in a heated glass round bottom flask equipped with a condenser. The excess amount of methyl chloride was removed by nitrogen purging. At a residence time of 3 hours the tertiary amine conversion to the quaternary ammonium chloride was 97.5%. The desired product was obtained in the form of a yellow clear liquid solution above 70° C.

EXAMPLE 2

The same equipment as described in example 1 was used for a continuous reaction of 102 g/hour diester of stearic acid and methyldiethanolamine/ethanol mixture with methyl chloride at 100° C. and 20 bar. The reactant tertiary amine/ methyl chloride molar ratio was 1:1.6 (MW amine=598) and the ethanol content was 15% counted on tertiary amine. At a residence time of 2 hours the tertiary amine conversion to the quaternary ammonium chloride was 97%. The desired product was obtained in the form of a slightly yellow clear liquid solution above 70° C.

EXAMPLE 3

The same equipment as described in example 1 was used for a continuous reaction of 68 g/hour diester of stearic acid and methyldiethanolamine with methyl chloride at 100° C. and 35 bar. The reactant tertiary amine/methyl chloride molar ratio was 1:2.5 (MW amine=598). At a residence time of 3 hours the tertiary amine conversion to the quaternary ammonium chloride was 96%. After depressurization sufficient ethanol was added to the product in order to obtain the desired activity, whereafter the remaining excess amount of methyl chloride was removed by nitrogen purging. The desired product was obtained in the form of a slightly yellow clear liquid solution above 70° C.

EXAMPLE 4

The same equipment as described in example 1 was used for a continuous reaction of 106 g/hour di(coco alkyl)methyl amine with methyl chloride at 10° C. and 30 bar. The reactant tertiary amine/methyl chloride molar ratio was 1:2.35 (MW amine=397). At a residence time of 2 hours the tertiary amine conversion to the quaternary ammonium chloride was 98%. After depressurization ethanol was added to the product in order to obtain a solution, whereafter the remaining excess amount of methyl chloride was removed by nitrogen purging. The desired product was obtained in the form of a slightly yellow clear liquid solution above 70° C.

COMPARISON 1

The same equipment as described in example 1 was used for a continuous reaction of 68 g/hour diester of stearic acid and methyldiethanolamine/isopropanol mixture with methyl chloride at 100° C. and 20 bar. The reactant tertiary amine/methyl chloride molar ratio was 1:1.2 (MW amine=598) and the isopropanol content was 15% counted on tertiary amine. At a residence time of 3 hours the tertiary amine conversion to the quaternary ammonium chloride was 89%.

COMPARISON 2

The same equipment as described in example 1 was used for a continuous reaction of 68 g/hour diester of stearic acid and methyldiethanolamine/isopropanol mixture with methyl chloride at 100° C. and 7 bar. The reactant tertiary amine/methyl chloride molar ratio was 1:1.6 (MW amine=602) and the ethanol content was 15% counted on tertiary amine. At a residence time of 3 hours the tertiary amine conversion to the quaternary ammonium chloride was 88%.

COMPARISON 3

The same equipment as described in example 1 was used for a continuous reaction of 68 g/hour diester of stearic and methyldiethanolamine with methyl chloride at 100° C. and 20 bar. The reactant tertiary amine/methyl chloride molar ratio was 1:4 (MW amine=598). At a residence time of three hours the tertiary amine conversion to the quaternary ammonium chloride was 89%. In Example 3 a conversion of 96% was achieved with a molar ratio of only 1:2.5.

The invention claimed is:

1. A continuous process for manufacturing a quaternary ammonium compound which comprises reacting, at a temperature of from 50° C. to 140° C., a reaction mixture comprising tertiary amine and an alkyl halide, wherein said alkyl halide is dissolved in said reaction mixture, and wherein the reaction is performed in a tubular reactor containing internals that are promoting plug-flow behavior, said reaction conducted at a pressure from 12 to 65 bar and sufficient to keep the alkyl halide dissolved in the reaction mixture, the molar ratio between the tertiary amine and the alkyl halide being from 1:1.3 to 1:2.9.

2. The process of claim 1 wherein the pressure is from 15 to 55 bar and the molar ratio between the tertiary amine and the alkyl halide is 1:1.4 to 1:2.7.

3. The process of claim 1 wherein the reaction mixture is, except for the alkyl halide, free from solvents.

4. The process of claim 3 wherein the pressure is 30–50 bar.

5. The process of claim 1 wherein the alkyl halide is selected from the group consisting of methyl chloride, methyl bromide, ethyl chloride and mixtures thereof.

6. The process of claim 1 wherein the quaternary ammonium compound has the formula

$$R_1R_2R_3R_4N^+X^- \quad (I)$$

where $R_1$ is a hydrocarbyl group containing 1–22 carbon atoms; $R_2$ and $R_3$ are the same or different hydrocarbyl groups containing 1–22 carbon atoms or a group $(AO)_yH$, where AO is an alkyleneoxy group with 2 or 3 carbon atoms and y is a number between 1–50;

$R_4$ is an alkyl group containing 1–4 carbon atoms and $X^-$ is a halide anion.

7. The process of claim 1 wherein the quaternary ammonium compound has the formula

$$R_5R_6R_7N^+(C_pH_{2p})(OA)_zQ\text{-}R_8X^- \quad (II)$$

where $R_5$ and $R_6$ independently is an alkyl group containing 1–6 carbon atoms; $R_7$ is—$(C_pH_{2p})(OA)_zQ\text{-}R_8$ or a hydrocarbyl group with 1–22 carbon atoms; $R_8$ is a hydrocarbyl group with 1–22 carbon atoms; Q is

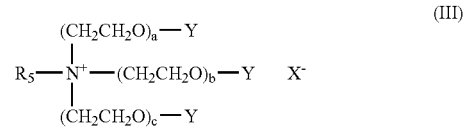

p is a number from 1 to 6, CA is an oxyalkylene group with 2 or 3 carbon atoms, z is a number between 0 and 50; $R_9$ is H or a hydrocarbyl group with 1–22 carbon atoms, and $X^-$ is a halide anion.

8. The process of claim 1 wherein the quaternary ammonium compound has the formula

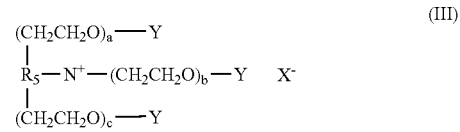

where each Y independently is H or —C(=O)—$R_8$, $\Sigma a+b+c$ is 3–50 and $R_5$ is an alkyl group containing 1–6 carbon atoms, $R_8$ is a hydrocarbyl group with 1–22 carbon atoms and $X^-$ is a halide anion.

* * * * *